United States Patent
Mantani et al.

(10) Patent No.: US 8,816,138 B2
(45) Date of Patent: Aug. 26, 2014

(54) METHOD FOR PRODUCING 3-CHLORO-PENTAFLUOROPROPENE

(75) Inventors: Toshiya Mantani, Settsu (JP); Emi Mantani, legal representative, Toyonaka (JP); Shinsuke Ohshita, Settsu (JP); Yuichi Hashikawa, Osaka (JP); Masahiro Kondo, Settsu (JP); Takashi Yoshimura, Settsu (JP); Noriyuki Shinoki, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 13/638,302

(22) PCT Filed: Mar. 28, 2011

(86) PCT No.: PCT/JP2011/057676
§ 371 (c)(1),
(2), (4) Date: Sep. 28, 2012

(87) PCT Pub. No.: WO2011/122573
PCT Pub. Date: Oct. 6, 2011

(65) Prior Publication Data
US 2013/0023704 A1    Jan. 24, 2013

(30) Foreign Application Priority Data

Mar. 29, 2010 (JP) ................................ 2010-075927
Nov. 10, 2010 (JP) ................................ 2010-252375

(51) Int. Cl.
*C07C 17/093* (2006.01)
*C07C 21/18* (2006.01)
*C07C 17/16* (2006.01)

(52) U.S. Cl.
CPC .................................. *C07C 17/093* (2013.01)
USPC ............................. 570/142; 570/136; 570/231

(58) Field of Classification Search
CPC .................................................. C07C 17/093
USPC ......................................... 570/142, 136, 231
See application file for complete search history.

(56) References Cited

U.S. PATENT DOCUMENTS 3,047,639 A     7/1962  Cunningham et al.
7,279,571 B2 *  10/2007 Gyollai et al. ................ 540/456

FOREIGN PATENT DOCUMENTS

JP    61-118333 A    6/1986
JP    2009-167120 A  7/2009

OTHER PUBLICATIONS

Banks, R. E. et al. Journal of Fluorine Chemistry "Perfluoroallyl fluorosulphonate" 1982, 20, 1133-1134.*
Setti, E L. et al. J. Org. Chem. "Nucleophilic SN2 displacement on (pivaloyloxy)methyl 6α-[(fluorosulfonyl)oxy]penicillanate" 1986, 51, 3217-3219.*
Albert L. Henne, et al.; "Perfluorinated Olefins"; Journal of the American Chemical Society; 1948; vol. 70; pp. 130-132.
Arnold H. Fainberg, et al.; "Some Reactions of Fluorinated Allyl Iodides"; Journal of the American Chemical Society; 1957; vol. 79; pp. 4170-4174.
Ronald E. Banks, et al.; "Perfluoroallyl Fluorosulphonate" Journal of Fluorine Chemistry; vol. 20 (1982); pp. 133-135.
English translation of International Preliminary Report on Patentability and Written Opinion of the ISA issued Oct. 23, 2012 for corresponding International Application No. PCT/JP2011/057676.

* cited by examiner

*Primary Examiner* — Fereydoun G Sajjadi
*Assistant Examiner* — Medhanit Bahta
(74) *Attorney, Agent, or Firm* — Sughrue Mion, PLLC

(57) ABSTRACT

The present invention provides a method for producing 3-chloro-pentafluoropropene at a high yield through one reaction step of chlorinating perfluoroallyl fluorosulfate. The present invention directs to a method for producing 3-chloro-pentafluoropropene, including the step of bringing perfluoroallyl fluorosulfate and an onium chloride compound into contact with each other to produce the 3-chloro-pentafluoropropene.

5 Claims, No Drawings

METHOD FOR PRODUCING 3-CHLORO-PENTAFLUOROPROPENE

CROSS REFERENCE TO RELATED APPLICATIONS

This application is a National Stage of International Application No. PCT/JP2011/057676 filed Mar. 28, 2011, claiming priority based on Japanese Patent Application Nos. 2010-075927 filed Mar. 29, 2010 and JP 2010-252375 filed Nov. 10, 2010, the contents of all of which are incorporated herein by reference in their entirety.

TECHNICAL FIELD

The present invention relates to a method for producing 3-chloro-pentafluoropropene.

BACKGROUND ART

3-Chloro-pentafluoropropene (hereinafter also referred to as "CPFP") is an important intermediate which can be derived as a material monomer of various fluorine compounds such as a fluororesin used for, for example, an ion exchange resin or a polymer electrolyte film.

Various methods for producing CPFP have been developed. Known examples include a method of pyrolyzing chlorotrifluoroethylene (e.g., Patent Document 1); a method of performing fluorination of 1,1,1,2,3,3,3-heptachloro-2-fluoropropane, and then performing dechlorination (e.g., Non-Patent Document 1); and a method of dechlorinating 1,2,3-trichloropentafluoropropane that is produced from chloroform and tetrachloroethylene through addition reaction, fluorination reaction, and the like reaction (e.g., Patent Document 2).

Another known method for synthesizing CPFP is a method of chlorinating 3-iodo-pentafluoropropene or 3-bromo-pentafluoropropene (Non-Patent Document 2).

Non-Patent Document 3 describes production of 3-iodo-pentafluoropropene and 3-bromo-pentafluoropropene from perfluoroallyl fluorosulfate.

Patent Document 1: U.S. Pat. No. 3,047,639
Patent Document 2: JP 61-118333 A
Non-Patent Document 1: Journal of American Chemical Society, Vol. 70, 1948, p. 130
Non-Patent Document 2: Journal of American Chemical Society, Vol. 79, 1957, pp. 4170-4174
Non-Patent Document 3: Journal of Fluorine Chemistry, Vol. 20, 1982, pp. 132-134

SUMMARY OF THE INVENTION

However, the methods described in Patent Documents 1 and 2 and Non-Patent Documents 1 and 2 require many reaction steps. For example, chlorination by the method of Non-Patent Document 2 requires the step of producing 3-iodo-pentafluoropropene or 3-bromo-pentafluoropropene from material monomers, and the step of chlorination.

As above, production of CPFP by a conventional method requires many reaction steps, and is thus accompanied by a low CPFP yield. Hence, these methods can be further improved in terms of productivity. The methods also have problems such as generation of zinc chloride as a by-product, and are therefore not suitable for large-scale synthesis. The method taught in Patent Document 1 can also be further improved in the yield that is decreased because of various by-products generated upon pyrolysis.

Non-Patent Document 3 does not teach a method for producing 3-chloro-pentafluoropropene. Non-Patent Document 3 describes production of 3-iodo-pentafluoropropene from perfluoroallyl fluorosulfate through iodination using potassium iodide, and describes production of 3-bromo-pentafluoropropene from perfluoroallyl fluorosulfate through bromination using potassium bromide. However, the method does not produce 3-chloro-pentafluoropropene even when potassium chloride is used instead of potassium iodide or potassium bromide to chlorinate perfluoroallyl fluorosulfate.

The present invention provides a method for producing CPFP at a high yield through one reaction step of chlorinating perfluoroallyl fluorosulfate.

The present invention relates to a method for producing 3-chloro-pentafluoropropene (perfluoroallyl chloride), including the step of bringing perfluoroallyl fluorosulfate and an onium chloride compound into contact with each other to produce the 3-chloro-pentafluoropropene.

The present invention is described in detail below.

The method for producing 3-chloro-pentafluoropropene according to the present invention includes the step of bringing perfluoroallyl fluorosulfate and an onium chloride compound into contact with each other to produce the 3-chloro-pentafluoropropene. Bringing perfluoroallyl fluorosulfate and an onium chloride compound into contact with each other enables to produce the 3-chloro-pentafluoropropene through one reaction step of chlorinating the perfluoroallyl fluorosulfate. Since the production involves only one reaction step, the method exhibits an excellent yield.

Further, the production method of the present invention enables to produce 3-chloro-pentafluoropropene from perfluoroallyl fluorosulfate through one reaction step without use of heavy metal. Accordingly, the production step is simple and the cost can be reduced. Also, no halogenated metal is generated, and thus industrial waste problems do not arise.

Up until now, no reports have been made on the method of directly chlorinating perfluoroallyl fluorosulfate, and the present inventors are the first to find out that bringing perfluoroallyl fluorosulfate and an onium chloride compound into contact with each other enables to produce 3-chloro-pentafluoropropene at a high yield through one step.

The perfluoroallyl fluorosulfate is a compound represented by the following formula:

$CF_2=CFCF_2OSO_2F.$

Examples of the onium chloride compound include compounds of an onium cation and a chloride ion. Examples of the onium cation include ones containing a hetero atom and a hydrocarbon group such as an alkyl group and a phenyl group bonded thereto. Examples of the hetero atom include nitrogen, phosphorus, sulfur, oxygen, selenium, tin, iodine, and antimony. Among these, the hetero atom is preferably nitrogen, phosphorus, sulfur, or oxygen, more preferably nitrogen or phosphorus, and still more preferably nitrogen.

The onium chloride compound is preferably a hydrochloride. For example, in the case that the hetero atom is a nitrogen atom, the onium chloride compound is preferably a salt of an amine and hydrogen chloride. Here, the amine is one in which not less than one hydrogen atom constituting ammonia is replaced by a hydrocarbon such as an alkyl group and a phenyl group.

The onium chloride compound may be a salt (heterocyclic onium chloride compound) of a cation having a heterocyclic structure and a chloride ion. The heterocyclic onium chloride compound is preferably a salt of hydrogen chloride and a heterocyclic nitrogen compound, in which not less than one carbon atom of benzene or cyclohexane is replaced by a nitrogen atom.

The number of atoms constituting a heterocyclic ring is preferably 3 to 6, and more preferably 5 or 6. The heterocyclic ring should include not less than one hetero atom. The heterocyclic ring may include not less than two hetero atoms, but the number of hetero atoms constituting one heterocyclic ring is preferably one. Examples of the hetero atom include the same ones as above, and a nitrogen atom is preferred among these hetero atoms.

The onium chloride compound is preferably liquid at temperatures for bringing perfluoroallyl fluorosulfate and the onium chloride compound into contact with each other. The liquid form allows chlorination reaction to efficiently proceed to further increase the CPFP yield.

In terms of efficient chlorination of perfluoroallyl fluorosulfate, the onium chloride compound is preferably capable of being dissolved in perfluoroallyl fluorosulfate.

Examples of the onium chloride compound include ammonium chloride compounds, phosphonium chloride compounds, sulfonium chloride compounds, and oxonium chloride compounds. Each of these may be used alone, or two or more of these may be used in combination.

Examples of the ammonium chloride compounds include a salt of a chloride ion and an ammonium ion. The ammonium ion is a primary, secondary, tertiary, or quaternary ammonium ion, and is preferably a tertiary or quaternary ammonium ion. More specifically, an ammonium ion containing a C1 to C20 alkyl group, a C6 to C30 aryl group which may have a substituent, or a C7 to C13 aralkyl group which may have a substituent is preferred. In the case that the ammonium chloride compound is ammonium chloride, bringing perfluoroallyl fluorosulfate and ammonium chloride into contact with each other does not allow chlorination reaction to efficiently proceed, and thus 3-chloro-pentafluoropropene cannot be produced at a high yield.

The examples of the ammonium chloride compounds also include a salt of hydrogen chloride and a heterocyclic nitrogen compound which may have a substituent. The substituent that the heterocyclic nitrogen compound may have is preferably a straight chain or branched C1 to C6 alkyl group, a straight chain or branched C1 to C6 alkoxy group, or a halogen atom.

The salt of hydrogen chloride and a heterocyclic nitrogen compound is preferably a salt of hydrogen chloride and a heterocyclic nitrogen compound, in which not less than one carbon atom constituting the ring of a cyclic compound such as benzene or cyclohexane is replaced by a nitrogen atom. The salt of hydrogen chloride and a heterocyclic nitrogen compound is more preferably at least one compound selected from the group consisting of piperidine hydrochloride, pyridine hydrochloride, pyrrolidine hydrochloride, quinoline hydrochloride, and 1-ethyl-3-methylimidazolidinium chloride.

A preferable example of the phosphonium chloride compounds is a salt of a chloride ion and a phosphonium ion. The phosphonium ion is a quaternary phosphonium ion, and is preferably a C1 to C20 alkyl group, a C6 to C30 aryl group which may have a substituent, or a C7 to C13 aralkyl group which may have a substituent.

A preferable example of the sulfonium chloride compounds is a salt of a chloride ion and a sulfonium ion, and examples thereof include a tertiary sulfonium salt such as methylmethionine sulfonium chloride.

A preferable example of the oxonium chloride compounds is a salt of a chloride ion and an oxonium ion.

The onium chloride compound is preferably at least one selected from the group consisting of an ammonium chloride compound and a phosphonium chloride compound, and is more preferably an ammonium chloride compound.

The onium chloride compound is at least one selected from the group consisting of
a compound represented by the following formula (1):

wherein X is nitrogen or phosphorus, and $R^1$, $R^2$, $R^3$, and $R^4$ are the same as or different from each other, each being a hydrogen atom, a C1 to C20 alkyl group which may have a substituent, a C7 to C13 aralkyl group which may have a substituent, or a C6 to C30 aryl group which may have a substituent, provided that not all of $R^1$, $R^2$, $R^3$, and $R^4$ are a hydrogen atom, and
a salt of hydrogen chloride and a heterocyclic nitrogen compound which may have a substituent.

The statement "not all of $R^1$, $R^2$, $R^3$, and $R^4$ are a hydrogen atom" means that at least one of $R^1$, $R^2$, $R^3$, and $R^4$ is a C1 to C20 alkyl group, a C7 to C13 aralkyl group which may have a substituent, or a C6 to C30 aryl group which may have a substituent.

The alkyl group in formula (1) is a C1 to C20 alkyl group, preferably a C1 to C10 alkyl group, and more preferably a C1 to C5 alkyl group. The alkyl group may be a straight chain alkyl group, or a branched alkyl group.

The aryl group in formula (1) is a C6 to C30 aryl group, and is preferably a C6 to C10 aryl group. Specifically, the aryl group is preferably at least one group selected from the group consisting of a phenyl group, a tolyl group, a xylyl group, a naphthyl group, and an anthranil group.

The aralkyl group in formula (1) is a C7 to C13 aralkyl group. Specifically, the aralkyl group is preferably at least one group selected from the group consisting of a benzyl group, a phenethyl group, and a naphthyl methyl group.

The alkyl group, the aryl group, or the aralkyl group may have a substituent, and the substituent is preferably a C1 to C6 alkyl group, a C1 to C6 alkoxy group, a cyano group, or a halogen atom.

The X in formula (1) is more preferably nitrogen.

In the case that X is a nitrogen atom, specific examples of the compound represented by formula (1) include quaternary ammonium salts such as tetrabutylammonium chloride, trioctylmethylammonium chloride, trimethylphenylammonium chloride, tetraphenylammonium chloride, (methoxymethyl) triphenylammonium chloride, benzyl trimethyl ammonium chloride, 1-ethylpyridinium chloride, and 1-ethyl-3-methylimidazolidinium chloride; tertiary amine hydrochlorides such as triethylamine hydrochloride, trimethylamine hydrochloride, and pyridine hydrochloride; secondary amine hydrochlorides such as diethylamine hydrochloride; and primary amine hydrochlorides such as ethylamine hydrochloride. Particularly, at least one selected from the group consisting of tetrabutylammonium chloride and triethylamine hydrochloride is preferred.

In the case that X is a phosphorus atom, specific examples of the compound represented by formula (1) include tetrabutylphosphonium chloride, cyanomethyl tributylphosphonium chloride, benzyltriphenylphosphonium chloride, tetraphenylphosphonium chloride, and (methoxymethyl)triphenylphosphonium chloride. Particularly, tetraphenylphosphonium chloride is preferred.

The compound represented by formula (1) contains a hydrogen atom as any one of $R^1$ to $R^4$, is preferably a tertiary amine hydrochloride containing alkyl groups as any three of $R^1$ to $R^4$, and is more preferably a triethylamine hydrochloride in terms of inexpensiveness and easy availability.

In the case of bringing the compound represented by formula (1) and perfluoroallyl fluorosulfate into contact with each other, 3-chloro-pentafluoropropene can be produced through a reaction represented by the following scheme:

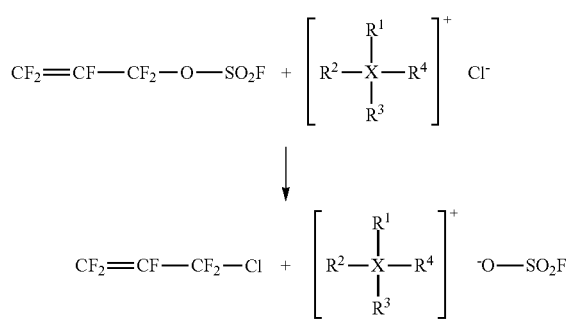

wherein X, $R^1$, $R^2$, $R^3$, and $R^4$ are the same as above.

Examples of the salt of a heterocyclic nitrogen compound and hydrogen chloride include the same ones as those described above.

The onium chloride compound is preferably at least one selected from the group consisting of a compound represented by the above formula (1) and a salt of hydrogen chloride and a heterocyclic nitrogen compound which may have a substituent. The onium chloride compound is more preferably a compound represented by the above formula (1). In the compound represented by the above formula (1), $R^1$, $R^2$, $R^3$, and $R^4$ are the same as or different from each other, and each of these is preferably a hydrogen atom or a C1 to C20 alkyl group, more preferably a hydrogen atom or a C1 to C10 alkyl group, and still more preferably a hydrogen atom or a C1 to C5 alkyl group.

The method of bringing perfluoroallyl fluorosulfate and an onium chloride compound into contact with each other is not particularly limited as long as the perfluoroallyl fluorosulfate and the onium chloride compound come into contact with each other. Examples of the method include a method of dropping perfluoroallyl fluorosulfate in a reaction vessel charged with an onium chloride compound; and a method of charging a reaction vessel with an onium chloride compound and perfluoroallyl fluorosulfate, and stirring the mixture. In terms of easy control of the reaction conditions, the method of dropping perfluoroallyl fluorosulfate is preferred.

The onium chloride compound may be brought into contact with perfluoroallyl fluorosulfate in the state of being dissolved in a solvent, or may be brought into contact with perfluoroallyl fluorosulfate in the absence of a solvent.

The contact between perfluoroallyl fluorosulfate and an onium chloride compound may be performed in a solvent or in the absence of a solvent. Usually, such contact in the absence of a solvent has been considered to result in an insufficient yield. However, the present invention enables to produce CPFP at a sufficiently high yield even in the case of achieving the contact in the absence of a solvent.

The solvent is preferably an organic solvent or an ionic liquid. The organic solvent or the ionic liquid is more preferably one that does not dissociate protons. The organic solvent or the ionic liquid may contain water to the extent that the effects of the present invention are not deteriorated. Still, it is preferable that the organic solvent or the ionic liquid substantially be free from water. This is because the water contained may possibly cause hydrolysis of perfluoroallyl fluorosulfate as a raw material instead of the desired reaction. In the case of employing a step such as water washing or distillation for isolation of CPFP, a water-soluble solvent having a higher boiling point than CPFP by not less than 50° C. is preferred.

Examples of such an organic solvent include ethers such as diethyl ether, ethyl methyl ether, diisopropyl ether, dibutyl ether, dibenzyl ether, diphenyl ether, oxetane, tetrahydrofuran, tetrahydropyran, and dioxane; esters such as methyl acetate, ethyl acetate, propyl acetate, isopropyl acetate, butyl acetate, isobutyl acetate, pentyl acetate, and isopentyl acetate; ketones such as acetone, methyl ethyl ketone, methyl butyl ketone, methyl isobutyl ketone, and cyclohexanone; glycol ethers such as ethylene glycol monomethyl ether, ethylene glycol monoethyl ether, ethylene glycol monobutyl ether, ethylene glycol dimethyl ether (monoglyme), diethylene glycol dimethyl ether (diglyme), triethylene glycol dimethyl ether (triglyme), and tetraethylene glycol dimethyl ether (tetraglyme); nitriles such as acetonitrile, propionitrile, and benzonitrile; sulfoxides such as dimethyl sulfoxide; acid amides such as N,N-dimethylformamide and N,N-dimethylacetamide; and mixtures thereof.

The volume of the solvent is preferably 0 to 200%, and more preferably 0 to 20% of the volume of perfluoroallyl fluorosulfate, for an increase in the stirring efficiency. The lower limit of the volume of the solvent may be 1% of the perfluoroallyl fluorosulfate used.

The temperature for the contact of perfluoroallyl fluorosulfate and an onium chloride compound is preferably −20° C. to 50° C., and more preferably 0° C. to 30° C., for example. The temperatures in the above range are preferred in terms of suppression of the pressure on the reaction vessel and rapid reaction.

The reaction time is not particularly limited because it depends on the reaction conditions such as the kind of the solvent and the temperature, but the reaction time is usually set to about 0.01 to 50 hours, and preferably to about 0.1 to 15 hours for sufficient reaction progress.

The reaction pressure is not particularly limited, and can be −0.01 to 1 MPa, for example. In terms of simplification of the production steps, the atmospheric pressure (1 atmosphere) is also preferred.

Since the reaction between perfluoroallyl fluorosulfate and an onium chloride compound is a reversible reaction, the onium chloride compound is preferably used in excess relative to the perfluoroallyl fluorosulfate. However, the onium chloride compound is a solid or a highly viscous liquid, and thus the amount of the onium chloride is preferably as small as possible for an increase in the stirring efficiency. For this reason, the amount of the onium chloride compound to be brought into contact with the perfluoroallyl fluorosulfate is preferably 1 to 3 molar equivalent to the perfluoroallyl fluorosulfate.

The resulting 3-chloro-pentafluoropropene may be purified by a known method such as distillation and column chromatography. The present invention may relate to a production method including the step of bringing perfluoroallyl fluorosulfate and an onium chloride compound into contact with each other in a reaction solvent to produce a liquid containing 3-chloro-pentafluoropropene, and the step of distilling the liquid. The distillation enables to produce high purity 3-chloro-pentafluoropropene. The obtained 3-chloropentafluoropropene can be identified by, for example, a gas chromatograph/mass spectrometer.

The production method of the present invention enables to produce CPFP at a high yield from perfluoroallyl fluorosulfate through one reaction step. The yield can be, for example, not less than 70%, or not less than 80%. The yield is a ratio of the obtained 3-chloro-pentafluoropropene (mole) to the perfluoroallyl fluorosulfate used (mole).

The reason that such a high yield can be achieved is not clear, but is presumably that the onium chloride compound is sufficiently dissolved in perfluoroallyl fluorosulfate under an anhydrous condition, and thus a separated chloride ion is bonded to the carbon atom at position 3 of the perfluoroallyl fluorosulfate to allow the ideal SN2' substitution reaction to proceed. The reaction results of a phosphonium salt having lower solubility than an ammonium compound also lead to the above presumption.

The 3-chloro-pentafluoropropene obtained by the above method is a compound useful as an intermediate which can be derived as a material monomer of a fluororesin used for, for example, an ion exchange resin or a polymer electrolyte film.

The polymer electrolyte film or the ion exchange resin is used as, for example, a film for the electrolyte of solid polyelectrolyte fuel cells, a film for lithium cells, a film for brine electrolysis, a film for water electrolysis, a film for hydrohalic acid electrolysis, a film for oxygen concentrator, a film for humidity sensors, or a film for gas sensors.

The present invention enables to produce CPFP at a high yield through one reaction step of chlorinating perfluoroallyl fluorosulfate. Since heavy metal is not used and no halogenated metal is generated, industrial waste problems do not arise.

MODES FOR CARRYING OUT THE INVENTION

Hereinafter, the present invention will be specifically described based on examples which, however, are not intended to limit the scope of the invention.

EXAMPLE 1

A 300-mL four-neck flask provided with a Dimroth condenser, a dropping funnel, and a thermometer was charged with triethylamine hydrochloride (97 g, 703 mmol) and 50 mL of diglyme, and the mixture was stirred by a magnetic stirrer. The Dimroth condenser was cooled using a −20° C. refrigerant, and the reaction flask was cooled to 0° C. in an ice bath. With the dropping funnel, perfluoroallyl fluorosulfate (135 g, 586 mmol) was dropped over about one hour in such a manner that the temperature in the flask was maintained at 10° C. or lower. After the dropping, the mixture was stirred for one hour. The Dimroth condenser was replaced by a Liebig distillation apparatus. The flask was allowed to reach room temperature (25° C.), and the resulting product (having a boiling point of 12° C.) was distilled. An amount of 100 mL of water was added to the flask to terminate the reaction. As a result, 90.7 g of the target perfluoroallyl chloride (purity: 99 GC %) was obtained as a distilled component (yield: 93%). The distillation residue was determined by NMR analysis to include carboxylic acids and ammonium fluorosulfate which were probably generated from hydrolysis of unreacted perfluoroallyl fluorosulfate in terminating the reaction, and an excess amount of triethylamine hydrochloride.

EXAMPLE 2

The reaction was achieved in the same manner as in Example 1, except that pyridine hydrochloride (81.0 g, 701 mmol) was used instead of triethylamine hydrochloride. As a result, 86.8 g of the target perfluoroallyl chloride was obtained from the perfluoroallyl fluorosulfate used (135 g, 586 mmol) (yield: 89%).

EXAMPLE 3

The reaction was achieved in the same manner as in Example 1, except that aliquat 336 (trade name, 72.7 g, 180 mmol, a mixture of tri-n-octyl methyl ammonium chloride as a main component and tri-n-decyl methyl ammonium chloride) was used instead of triethylamine hydrochloride, and 54 g of acetone was used as a solvent. As a result, 11.9 g of the target perfluoroallyl chloride was obtained from the perfluoroallyl fluorosulfate used (31.1 g, 135 mmol) (yield: 53%).

EXAMPLE 4

The reaction was achieved in the same manner as in Example 1, except that a solvent was not used. As a result, 87.7 g of the target perfluoroallyl chloride was obtained from the perfluoroallyl fluorosulfate used (135 g, 586 mmol) (yield: 90%).

EXAMPLE 5

The reaction was achieved in the same manner as in Example 1, except that 50 mL of triethylamine fluorosulfate was used as a solvent. As a result, 89.8 g of the target perfluoroallyl chloride was obtained from the perfluoroallyl fluorosulfate used (135 g, 586 mmol) (yield: 92%).

COMPARATIVE EXAMPLE 1

The reaction was achieved in the same manner as in Example 1, except that ammonium chloride (37.4 g, 700 mmol) was used instead of triethylamine hydrochloride. The reaction hardly proceeded, and the amount of the obtained target perfluoroallyl chlorides was 3.5 g (yield: 3%).

COMPARATIVE EXAMPLE 2

The reaction was achieved in the same manner as in Example 1, except that potassium chloride (52.2 g, 700 mmol) was used instead of triethylamine hydrochloride. The reaction did not proceed at all, and perfluoroallyl fluorosulfate and potassium chloride, the raw materials, were recovered. The reaction mixture was filtered, and the filtrate was determined by NMR and GC analysis to include perfluoroallyl fluorosulfate, a raw material.

EXAMPLE 6

The reaction was achieved in the same manner as in Example 1, except that tetrabutylammonium chloride (14.5 g, 52.2 mmol) was used instead of triethylamine hydrochloride. As a result, 7.0 g of the target perfluoroallyl chloride was obtained from the perfluoroallyl fluorosulfate used (10.0 g, 43.5 mmol) (yield: 96.4%).

EXAMPLE 7

The reaction was achieved in the same manner as in Example 1, except that tetraphenylphosphonium chloride (24.5 g, 65.3 mmol) was used instead of triethylamine hydrochloride. As a result, 2.4 g of the target perfluoroallyl chloride was obtained from the perfluoroallyl fluorosulfate used (10.0 g, 43.5 mmol) (yield: 32.5%).

INDUSTRIAL APPLICABILITY

3-Chloro-pentafluoropropene obtained by the production method of the present invention is suitably usable as an intermediate which can be derived as a material monomer of a fluororesin used for, for example, an ion exchange resin or a polymer electrolyte film.

The invention claimed is:

1. A method for producing 3-chloropentafluoropropene, comprising the step of
bringing perfluoroallyl fluorosulfate and an onium chloride compound into contact with each other to produce the 3-chloropentafluoropropene,
wherein the onium chloride compound is at least one selected from the group consisting of a salt of an amine and hydrogen chloride, a salt of hydrogen chloride and a substituted or unsubstituted heterocyclic nitrogen compound, and a phosphonium chloride compound.

2. The method for producing 3-chloropentafluoropropene according to claim 1,
wherein the onium chloride compound is at least one selected from the group consisting of
a compound of the following formula (1):

wherein X is nitrogen or phosphorus, and in the case where X is nitrogen, any one of $R^1$ to $R^4$ is a hydrogen atom, and any three of $R^1$ to $R^4$ are the same as or different from each other, each being a substituted or unsubstituted C1 to C20 alkyl group, and in the case where X is phosphorous, $R^1$, $R^2$, $R^3$, and $R^4$ are the same as or different from each other, each being a hydrogen atom, a substituted or unsubstituted C1 to C20 alkyl group, a substituted or unsubstituted C7 to C13 aralkyl group which may have a substituent, or a C6 to C30 aryl group, provided that not all of $R^1$, $R^2$, $R^3$, and $R^4$ are a hydrogen atom, and
a salt of hydrogen chloride and a substituted or unsubstituted heterocyclic nitrogen compound which may have a substituent.

3. The method for producing 3-chloropentafluoropropene according to claim 1,
wherein the onium chloride compound is of the following formula (1):

wherein X is nitrogen or phosphorus, and in the case where X is nitrogen, any one of $R^1$ to $R^4$ is a hydrogen atom, and any three of $R^1$ to $R^4$ are the same as or different from each other, each being a substituted or unsubstituted C1 to C20 alkyl group, and in the case where X is phosphorous, $R^1$, $R^2$, $R^3$, and $R^4$ are the same as or different from each other, each being a hydrogen atom, a C 1 to C20 alkyl group, a substituted or unsubstituted C7 to C13 aralkyl group, or a substituted or unsubstituted C6 to C30 aryl group, provided that not all of $R^1$, $R^2$, $R^3$, and $R^4$ are a hydrogen atom.

4. The method for producing 3-chloropentafluoropropene according to claim 1,
wherein an amount of the onium chloride compound to be brought into contact with the perfluoroallyl fluorosulfate is 1 to 3 molar equivalent to the perfluoroallyl fluorosulfate.

5. The method for producing 3-chloropentafluoropropene according to claim 1,
wherein the contact is achieved at −20° C. to 50° C.

* * * * *